(12) United States Patent
Carter et al.

(10) Patent No.: US 11,986,284 B2
(45) Date of Patent: May 21, 2024

(54) CAPNOMETER

(71) Applicant: CAMBRIDGE RESPIRATORY INNOVATIONS LTD, Cambridge (GB)

(72) Inventors: Julian Carter, Cambridge (GB); Jeremy Walsh, Cambridge (GB); Russell Overend, Glasgow (GB); Craig Whitehill, Glasgow (GB); Colin Phimister, Glasgow (GB)

(73) Assignee: CAMBRIDGE RESPIRATORY INNOVATIONS LTD, Cambridge (GB)

( * ) Notice: Subject to any disclaimer, the term of this patent is extended or adjusted under 35 U.S.C. 154(b) by 831 days.

(21) Appl. No.: 16/981,244

(22) PCT Filed: Mar. 13, 2019

(86) PCT No.: PCT/IB2019/052040
§ 371 (c)(1),
(2) Date: Sep. 15, 2020

(87) PCT Pub. No.: WO2019/175800
PCT Pub. Date: Sep. 19, 2019

(65) Prior Publication Data
US 2021/0038118 A1    Feb. 11, 2021

(30) Foreign Application Priority Data

Mar. 15, 2018    (GB) ...................................... 1804172

(51) Int. Cl.
*A61B 5/083*    (2006.01)
*A61B 5/08*    (2006.01)
(Continued)

(52) U.S. Cl.
CPC ............ *A61B 5/0836* (2013.01); *A61B 5/082* (2013.01); *G01N 21/3504* (2013.01);
(Continued)

(58) Field of Classification Search
CPC ....... A61B 5/0836; A61B 5/082; A61B 5/097; G01N 21/3504; G01N 33/497; G01N 2201/0634; G01N 2201/0636
See application file for complete search history.

(56) References Cited

U.S. PATENT DOCUMENTS 4,350,412 A * 9/1982 Steenblik ............. G02B 17/006
126/684
4,775,967 A * 10/1988 Shimada ................. G11B 7/08
369/44.41

(Continued)

FOREIGN PATENT DOCUMENTS

GB    2533125 A *    6/2016    ........... A61B 5/0059

OTHER PUBLICATIONS

Search Report for International Patent Application PCT/IB2019/052040, mailed on Sep. 19, 2019.

*Primary Examiner* — Eric F Winakur
*Assistant Examiner* — Abid A Mustansir
(74) *Attorney, Agent, or Firm* — FRESH IP PLC; Clifford D. Hyra; Aubrey Y. Chen

(57) ABSTRACT

We describe a capnometer for detecting a concentration of a component in a gas, wherein said gas is inhaled and/or exhaled by a patient, said capnometer comprising: an air flow region through which said gas passes to and/or from said patient's lung; a mid-IR semiconductor emitter configured to provide IR light at a wavelength in the range 3-5 μm; a mid-IR semiconductor detector to detect said IR light; a reflector to reflect said IR light emitted by said emitter; wherein said emitter, said detector and said reflector are
(Continued)

arranged such that said IR light emitted by said emitter passes through said air flow region via said reflector to said detector. The reflector is selected from a Fresnel reflector and a reflective diffractive optical element, such as a Fresnel zone plate.

20 Claims, 6 Drawing Sheets

(51) Int. Cl.
  *G01N 21/3504* (2014.01)
  *G01N 33/497* (2006.01)
(52) U.S. Cl.
  CPC ... *G01N 33/497* (2013.01); *G01N 2201/0634* (2013.01); *G01N 2201/0636* (2013.01)

(56) References Cited

U.S. PATENT DOCUMENTS

| | | | |
|---|---|---|---|
| 9,510,774 B2 | 12/2016 | Russell | |
| 10,113,954 B2 | 10/2018 | Hayashi et al. | |
| 2012/0242980 A1* | 9/2012 | Russell | A61B 5/082 |
| | | | 356/51 |
| 2017/0059477 A1* | 3/2017 | Feitisch | G01N 21/39 |

* cited by examiner

CAPNOMETER

FIELD OF THE INVENTION

This invention generally relates to a capnometer, in particular a capnometer utilising a reflecting geometry, and methods for determining a $CO_2$ level in a gas using a capnometer.

BACKGROUND TO THE INVENTION

Measurements of concentration of certain gases in breath can be made using non-dispersive infrared techniques. The most common is the measurement of carbon dioxide using the 4.26 μm absorption band, examples being disclosed by Andros Inc in U.S. Pat. Nos. 4,423,739A, 4,200,791A and 4,013,260A and Hitachi Ltd in U.S. Pat. No. 3,893,770. By making measurements successively it is possible to record the variation of carbon dioxide in breath as a function of time. These devices, known as capnometers, are useful in providing insight into both the ventilation and perfusion of air in the lungs.

It is beneficial to be able to measure the concentration of gas with a high accuracy over a wide concentration range and at high temporal resolution. Typically for measurements of carbon dioxide in breath the range of measurement can vary from the background level of carbon dioxide in air that we breathe in to the concentration of carbon dioxide dissolved in venous blood, which for acutely hypercapnic patients can exceed 10 kPa. When considering the requirement for temporal resolution of gas measurement in breath we must realise that the expiratory and inspiratory upstroke occur over a short fraction of a breath. Furthermore, for neonates the breath rate can be rapid—up to 60 breaths per minute. Therefore it is desirable to have detector response times of over 100 Hz. In addition, to prevent the loss of temporal information, it is necessary to make measurements close to the nose of mouth and therefore the sensor can be affected be condensation in breath.

It is also desirable to make these devices low cost and to allow for a low-cost replaceable breath tube, a disposable element that isolates the patient's breath from the body of the device, so that the device does not become contaminated.

The use of a reflecting geometry LED capnometer has been described in U.S. Pat. No. 5,261,415 and as described in US 2013/0271751 A1, WO 2007/091043 A1 and D. Gibson and C. MacGregor "A Novel Solid State Non-Dispersive Infrared CO2 Gas Sensor Compatible with Wireless and Portable Deployment", Sensors 2013, 13(6):7079-7103 (May 2013) and the Applicant's co-pending PCT Application Publication No. WO 2016/092308. The use of efficient mid-infrared LEDs and reflecting geometries as described therein can achieve high temporal resolution and high accuracy over a specific concentration range. However, the use of spherical/elliptical curved mirrors introduce a number of difficulties, namely they are difficult to heat uniformly to prevent condensation; the curvature can cause gas to be trapped in the apex that reduces the temporal resolution of the system and the single path length means the sensor is suited to a narrow range of gas concentration measurement. Also, the curved system does not lend itself to introducing a replaceable breath tube.

There is therefore a need to improve capnometers using a reflecting geometry.

SUMMARY OF THE INVENTION

According to a first aspect of the invention, there is therefore provided a capnometer for detecting a concentration of a component in a gas, wherein said gas is inhaled and/or exhaled by a patient, said capnometer comprising: an air flow region through which said gas passes to and/or from said patient's lung; a mid-IR semiconductor emitter configured to provide IR light at a wavelength in the range 3-5 μm; a mid-IR semiconductor detector to detect said IR light and a reflector to reflect said IR light emitted by said emitter; wherein said emitter, said detector and said reflector are arranged such that said IR light emitted by said emitter passes through said air flow region via said reflector to said detector characterised in that the reflector is selected from the group consisting of a Fresnel reflector and a reflective diffractive optical element.

The capnometer may be used to quantitatively measure the concentration (or associated temporal variation, as will be further described below) of a particular gas component in a gas mixture using the principle of non-dispersive IR absorption.

The reflecting geometry of the capnometer provides for low cost production and low power consumption. The inventors have realised that transmissive optics, rotating elements or beam splitter optics with filters, which are generally employed in a collimated optics geometry, may be made redundant in a capnometer by using the reflecting geometry. The capnometer may therefore be utilised to perform measurements in which an adjacent emitter/detector pair is arranged on one side of a gas sample volume and a reflecting surface is provided on the other side of the gas sample volume.

The reflecting geometry further allows for achieving an appropriate sampling length in order to achieve required signal-to-noise ratio in the detector at the gas concentration appropriate for lung function measurements. In the reflecting geometry, the sampling length may be determined by the distance between the emitter and the reflector as well as the distance between the reflector and the detector. In particular, the provision of a reflector as defined by the invention provides a substantially flatter geometry leading to a number of advantages, including being easier to heat uniformly, having a lower heat energy requirement, allowing the easier insertion of a replaceable breath tube with minimal dead space, dead space being gas outside of the breath tube that is sampled by the detector. In addition the flatter geometry provides a range of path lengths thereby increasing the range of gas concentration measurement of the capnometer. Furthermore, by using a reflecting focussing element based on diffraction there can be an advantage in reducing the requirement for placement accuracy of the reflector relative to the emitter and detector which can reduce the cost of device and make the measurement more accurate. Additionally, a reflector based on diffraction has more wavelength specificity thereby allowing the sensor to have more sensitivity to the target gas to be sampled.

The capnometer may be operated in a non-diverting or substantially non-diverting mode so that high temporal resolution may be achieved when the concentration of the component in the gas is determined.

The capnometer may be implemented in a way which allows the measurement of a gas concentration close to the oro-nasal orifices.

In a preferred embodiment of the capnometer, the detection of the concentration of the component in a gas comprises detecting a temporal variation of the concentration of the component.

It will be appreciated that a number of configurations may be employed using the reflective geometry.

In a preferred embodiment of the capnometer, the emitter is located at a first location on a first side of said air flow region, wherein said detector is located at a second location on a second side of said air flow region, wherein said first side is adjacent said second side, wherein said reflector is located at a third location on a third side of said air flow region, and wherein said third side is opposite said first side or opposite said second side. The reflector comprises at least one of a Fresnel reflector and a reflecting Fresnel zone plate.

The reflector is a Fresnel reflector or a reflective diffractive optical element. A Fresnel reflector may comprise of one or more cuts within a curved reflector that terminate on a single plane thereby reducing the thickness of the reflecting element. Preferably, at least four cuts are provided in concentric rings.

Alternatively, the reflector is a reflective diffractive optical element. For example, the reflector may comprise a Fresnel zone plate, reflective grating, a hologram or photon sieve. More preferably, the reflector comprises a Fresnel zone plate (FZP) having single or multiple phase levels. A FZP differs from a Fresnel reflecting lens in that the focussing of the light is achieved through diffraction. The diffractive elements are formed in thin films or directly onto the surface of a body and can be mass produced cheaply compared to conventional refractive or reflective optics. This enables the structures to have the flattest and thinnest geometry of a focussing element thereby providing the lowest dead space, improved heating uniformity and lower heating power and lower cost of materials. In addition the diffracting elements may be designed so that the sensitivity of the signal level received by the detector to location of the zone plate is reduced thereby increasing the accuracy of the device.

In one embodiment, a reflecting zone plate having multiple phase levels comprises a series of steps. Preferably, the series of steps approximate to the continuous phase change introduced by a curved reflector. The multiphase zone plate contains more than one step height. More preferably, the step heights introduce $<\pi/2$ phase change with no step height introducing greater than $2\pi$ of phase change. This limits the total height of the step and therefore limits the total thickness of the reflector substantially to this height. For mid-infrared wavelengths the step heights are $<0.5$ µm and the total step heights are $<5$ µm.

In a more preferred embodiment, the reflector comprises a Fresnel zone plate of a single phase level. A reflecting Fresnel zone plate comprises steps of a single height patterned on a surface and coated with a reflector such that the interference of wave fronts reflected from the surface of the zone plate maximises the flux of radiation on the detector. Typically, the height of the step is one quarter the wavelength of light. The particular pattern provided in the FZP may be optimised to maximise the radiation intensity arriving at the detector and depending on the position and size of the emitter and detector, the sampling size and other optical elements in the radiation path. In a conventional Fresnel zone plate the steps are arranged in concentric circles or ellipses, however those skilled in the art can calculate the arrangement of steps on the zone plate to achieve the maximum signal at the detector or a high signal level combined with a reduced sensitivity to zone plate placement relative to the emitter and detector. Alternative patterns of steps may be provided, for example in the form of a grating, hologram or photon sieve.

The material of the Fresnel reflector, FZP or other reflective diffractive optical element may be any suitable material for this application known in the art. Preferably, a Fresnel reflector is made from a high density polymer, more preferably being injection moulded. The reflector surface is provided by a coating of a thin metal film, for example being applied by evaporation, sputtering or other physical vapour deposition or via an electrochemical method. Examples of suitable metals include, but are not limited to, gold, silver and aluminium.

A Fresnel zone plate may also be fabricated from a high density polymer and injection moulding. The step arrangements/patterns may be fabricated in a master using silicon microfabrication techniques known to those skilled in the art, such as photolithography and etching of silicon dioxide, silicon nitride and silicon oxynitride layers grown by chemical vapour deposition (CVD) or plasma enhanced chemical vapour deposition (PECVD) on silicon. The master zone plate patterns may be used in the injection moulding tooling directly or used to make an electroformed mould insert, typically using electroplated nickel. The reflector surface is provided by a thin metal film as with the Fresnel lens, such as a coating of gold, silver or aluminium.

Preferably, the FZP is provided as a thin film single level phase FZP focussing element. A film FZP may be fabricated on a sheet using a hot embossing method. For example, a foil, such as a thin metal or polymer of PET or PEN is coated with an upper surface containing a thermosetting polymer capable of being moulded using a hot embedding roller. The foil may then be coated with a reflective coating as hereinbefore described and the FZP cut from the foil. The foil may incorporate a backside conducting element that may be attached to a current source using conductors.

In a preferred embodiment, the capnometer further comprises a breath tube, wherein the breath tube defines a channel between the emitter/detector and the Fresnel reflector, FZP or other reflective diffractive optical element for the air flow region. Preferably, the reflector has a planar surface. More preferably only a single reflector is required. Preferably, the breath tube is removable from the capnometer. A replaceable breath tube is useful for a multi-user device since it prevents transfer of disease between patients and is useful for a single-user device since any build-up of contamination in the optical path that reduces the signal level can be mitigated.

In embodiments of the capnometer which use a breath tube, the emitter, the detector and/or the Fresnel reflector, FZP or reflective diffractive optical element may be mounted in the breath tube. Where the breath tube is removable from the capnometer, exchanging the breath tube with emitter, detector and/or reflector may allow for minimising any contamination on the emitter, detector and/or reflector.

The breath tube is preferably formed from a high density polymer, preferably by injection moulding.

In another preferred embodiment, the capnometer may further comprise at least one optical layer between the emitter and the reflector and/or between the detector and the reflector for improving a collection efficiency of the IR light emitted by the emitter onto the detector. This optical layer may comprise a mid infrared transmissive material such as, but not limited to silicon. Other materials suitable for the optical layer will be known to those skilled in the art, and include, but are not limited to ZnS, ZnSe, Ge, chalocogenide glasses and certain polymers. It will be appreciated that where emitter and detector are arranged on the same side of the air flow region, the optical layer may be a single layer, or two separate layers between emitter/reflector and detector/reflector, respectively. Layer or layers may have anti-reflection coatings applied to their surfaces, thereby minimising or reducing reflection loss and maximising or increasing transmission through the layer or layers. The layers may also contain diffracting optical elements to improve the collection efficiency of the detector.

In a further preferred embodiment of the capnometer, the emitter and/or the detector are located external to the breath tube, and the breath tube comprises a first mid-IR transmissive portion, wherein the mid-IR transmissive portion is aligned with the emitter and the detector to allow mid-IR light to pass therethrough into and out of the breath tube. Preferably, the mid-IR transmissive portion comprises a separate window. It will be understood that if no separate window is exploited, the breath tube may be mid-IR transmissive at the portion which is aligned with the emitter and the detector. Where the mid-IR transmissive portion comprises a separate window, the capnometer preferably further comprises a seal arranged between the breath tube and the separate window. The seal may be suitable for preventing air surrounding the capnometer from penetrating into the air flow region where the gas is sampled.

The breath tube is provided with appropriate recesses formed therein for receipt of any components, such as the mid-IR transmissive portion. The components are secured therein by suitable means, such as adhesive.

The mid-IR transmissive portion may include an anti-reflection coating and/or an anti-fog coating. This may increase a collection efficiency of IR light emitted by the emitter onto the detector, and may therefore improve the signal-to-noise ratio as the coatings reduce scattering of IR light on the mid-IR transmissive portion. Alternatively, or additionally, the capnometer may further comprise a heater for heating the mid-IR transmissive portion. In this way, water condensation on the mid-IR transmissive portion may be prevented in order to increase the collection efficiency and hence the signal-to-noise ratio.

In addition to the mid-IR transmissive portion, the capnometer may further comprise an optical layer between the emitter and the reflector and/or between the detector and the reflector for improving a collection efficiency of the IR light emitted by the emitter onto the detector. It will be appreciated that where emitter and detector are arranged on the same side of the air flow region, the optical layer may be a single layer, or two separate layers between emitter/reflector and detector/reflector, respectively. Preferably, the optical layer comprises an anti-reflection coating and/or an anti-fog coating. More preferably, the capnometer may further comprise a second heater for heating the optical layer in order to avoid water condensation on the surface of the optical layer. It will be appreciated that the first heater and second heater may be integral. Furthermore, the mid-IR transmissive portion and the optical layer may, in embodiments, be integral.

As outlined above, the optical layer may comprise silicon, ZnS, ZnSe, Ge, chalocogenide glasses, certain polymers, or other materials known to those skilled in the art.

In a preferred embodiment of the invention, the Fresnel reflector, FZP or reflective diffractive optical element is formed as part of, or integral to, the breath tube whereas the emitter and the detector are external to the breath tube. In this embodiment, a single IR-transmissive window is provided in the breath tube opposite the reflector. Preferably, the reflector is provided with a heater, preferably being external to the breath tube. The use of a reflector within the breath tube provides a flat surface for contact with the heater, enabling more uniform heating of the reflector. More preferably, a single phase FZP is provided on a film, preferably with a backside laminated heater, and is attachable to the breath tube using a preformed recess in the tube, for example using a push-fit clip or other securing means.

In embodiments, the breath tube may comprise one or more alignment features for enabling the arrangement of the reflector with the emitter and the detector. Hence, these alignment features may improve the signal level and reproducibility of the measurements taken with the capnometer. The one or more alignment features may comprise alignment pins which may provide kinematic location of the capnometer component parts and ease of assembly.

Alternatively, in embodiments of the capnometer, the reflector is located external to the breath tube, and the breath tube comprises a second mid-IR transmissive portion, wherein the second mid-IR transmissive portion is aligned with the reflector to allow mid-IR light to pass therethrough into and out of the breath tube.

In embodiments of the capnometer, the emitter may be configured to provide the IR light at two or more different wavelengths in the range 3-5 µm, and the detector may be configured to detect the two or more different wavelengths for the signal processor. This embodiment may be particularly suitable for detecting different gases with different absorption peaks or generally different absorption spectra.

In a preferred embodiment, the capnometer further comprises a memory to store the level data output. This may allow for analysing the gas concentration and/or temporal variation of the gas concentration measured with the capnometer at a later stage.

In a preferred embodiment, the gas component to be detected in the gas mixture is $CO_2$.

In a further preferred embodiment of the capnometer, the emitter comprises a III-V mid-IR semiconductor emitter.

In another preferred embodiment of the capnometer, the detector comprises a III-V mid-IR semiconductor detector.

It will be appreciated that the type of emitter and detector may be determined by the gas and/or gas component to be sampled.

It will be important to obtain a sufficient temporal resolution of the measurements to allow the signal to convey enough information about a perfusion and a ventilation of lungs of a patient. The sample width may be reduced using cut down optics and/or a breath tube design to accelerate gas through the sampling area. Therefore, in a preferred embodiment of the capnometer, the air flow region may have a cross-sectional area which is reduced where the IR light passes through the air flow region.

The capnometer may be used in combination with a medical device, wherein the capnometer further comprises blocking means to inhibit air surrounding the capnometer from flowing into the medical device.

In a preferred embodiment of the capnometer, the emitter comprises a plurality of emitters, wherein each of the plurality of emitters emits light centred at a different, respective wavelength. This may allow different gases with different absorption spectra to be sampled with the capnometer. Furthermore, this embodiment allows for calibrating the device and/or determining when a measurement of a gas concentration is void.

In a further preferred embodiment, the detector comprises a plurality of detectors, wherein each of the plurality of detectors detects light at a different, respective range of wavelengths.

The design of the optical path is to ensure a good collection efficiency of the optical system, comprising emitter and detector, employed in the capnometer. The use of materials with low absorption at wavelengths where the component absorbs light (e.g. 4.26 µm for $CO_2$) may be preferable. Moreover, a high reflective surface of the reflector may be achieved by using, e.g. Au deposited by physical vapour deposition or electrochemical deposition.

The capnometer may also comprise a diversion device. For example, the capnometer may comprise a diversion device for blocking one of a first and a second air-flow path in the capnometer at a time, wherein the first air-flow path connects an inhaling/exhaling portion of the capnometer at which a user of the capnometer inhales/exhales air and an intake portion of the capnometer through which air enters the capnometer, and wherein the second air-flow path connects the inhaling/exhaling portion and an exit portion of the capnometer at which air exits the capnometer.

In a preferred embodiment of the capnometer, the diversion device comprises a diverting valve which is controlled by the inhalation/exhalation of air by the user. For example, during inhalation, the diverting valve may open the first air-flow path between the inhaling/exhaling portion and the intake portion of the capnometer, while it closes the second air-flow path between the inhaling/exhaling portion and the exit portion of the capnometer at the same time. The situation may be reversed during exhaling by the user, such that the connection between the inhaling/exhaling portion and the intake portion is closed, while the connection between the inhaling/exhaling portion and the exit portion is open. It will be appreciated that the opposite operation of the diverting valve may be employed, in which the first air-flow path is blocked during inhalation and the second air flow-path is open (and opposite during exhaling). The diverting valve may allow for a simple, reliable and cheap construction of the diversion device.

It will be understood that the diversion device may take other forms, which may be controlled by other means, such as electronic means.

Embodiments of the capnometer described herein may be combined with and/or incorporated into an inhaler. Therefore, there is provided an inhaler comprising a capnometer as described in any of the embodiments herein, wherein said capnometer is configured to monitor a $CO_2$ level in air inhaled through or exhaled through said inhaler.

The capnometer may also be configured to output gas concentration data from a gas inhaled/exhaled from a patient and be connected to a data processor configured to receive the gas concentration data. The gas concentration data may, in embodiments, be $CO_2$ gas concentration data. It will be understood that the processor for receiving the gas concentration data may be integral to the capnometer.

BRIEF DESCRIPTION OF THE DRAWINGS

These and other aspects of the invention will now be further described by way of example only, with reference to the accompanying figures, wherein like numerals refer to like parts throughout, and in which.

DETAILED DESCRIPTION OF PREFERRED EMBODIMENTS

Figure 1:
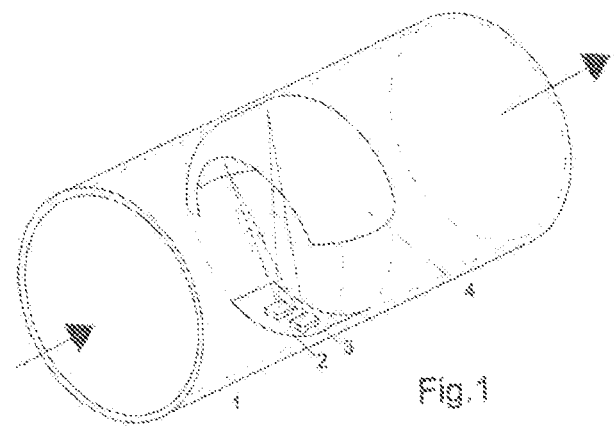
FIG. 1 shows a schematic illustration of components of a capnometer according to the prior art.

FIG. 1 shows a schematic illustration of components of a capnometer according to the prior art, such as that described in the Applicant's earlier co-pending Patent Application Publication No. WO 2016/092308. The device may be exploited to measure the concentration of a gas component, such as carbon dioxide in a sample gas (for example, exhaled air) flowing across an air flow region interposed between an emitter (2)/detector (3) pair and a reflector (4). In FIG. 1, an emitter (2)/detector (3) pair and a curved reflector (4) are incorporated into a breath tube (1) and are connected to a suitable electronic drive and detecting circuitry. The value of the detector current may be proportional to the emitter current and the amount of gas to be sampled in the sampling area.

The emitter (2) and/or the detector (3) of the capnometer may be composed of III-V semiconductors. It will be appreciated that materials suitable for emitter (2) and detector (3) will be known to those skilled in the art. Ideally, an emitter diode is designed to emit IR radiation centred around 4.26 μm and the detector (3) is a photo-diode which has a peak sensitivity centred around 4.26 μm.

The path length traversed by the IR light emitted by the emitter (2) and detected by the detector (3) via the reflector (4) is chosen such that the attenuation of the signal by absorption by $CO_2$ molecules is such that a change in intensity can be detected by the detector (3) for the concentration range that is appropriate for the gas stream. For human breath, the range of $CO_2$ concentration varies between the background $CO_2$ level which is inhaled by the human and over 10 kPa which is exhaled by the hypercapnic patients. For the mid-range of 5 kPa the distance traversed by the IR light may be approximately 20 mm.

Figure 2:
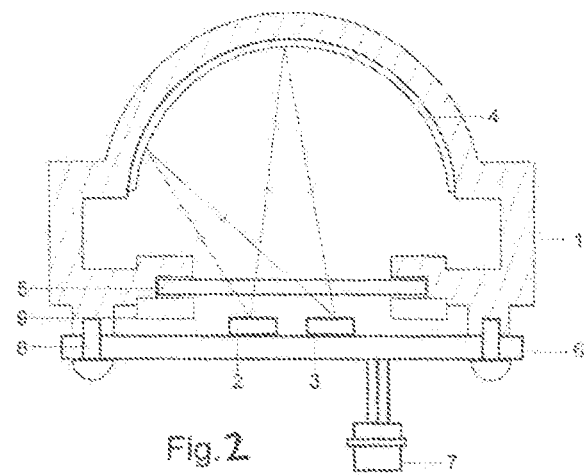
FIG. 2 shows a schematic of a capnometer comprising a silicon optic window according to the prior art.

FIG. 2 shows another capnometer according to the prior art. The capnometer incorporates a disposable breath tube (1) with a curved reflector (4) and an optical layer (5) which may comprise silicon. The optical layer (5) forms a seal with the breath tube (1). The purpose of the optical layer (5) comprising silicon is both to protect the emitter (2)/detector (3) pair from breath, e.g. to avoid a contamination of the emitter (2)/detector (3) pair, and to increase the collection efficiency of the system by directing more light emitted from the emitter (2) to impinge on the detector (3). Other materials suitable for the optical layer (5) will be known to those skilled in the art, and include, but are not limited to ZnS, ZnSe, Ge, chalocogenide glasses and certain polymers. The capnometer includes a seal (9) to prevent gas from the surrounding area from entering the sampling area. In the illustrated example, the seal (9) is arranged at two locations where the breath tube (1) and the optical layer (5) connect with each other. It will be appreciated that the seal (9) may be arranged at one or more locations. The seal (9) may be arranged on a side facing the air flow region where the breath tube (1) and the optical layer (5) connect, and/or on a side facing away from the air flow region (as shown in FIG. 2).

The emitter (2)/detector (3) pair are mounted on a printed circuit board (6) which may incorporate high precision locating lugs for locating pins (8) that are incorporated into the injection moulded breath tube (1). This allows for a high precision alignment of the emitter (2)/detector (3) pair to the curved reflector (4) so that high collection efficiency may be achieved. The printed circuit board (6) allows connection between the emitter (2)/detector (3) pair and a driving circuit. An electrical connector (7) is connected to the printed circuit board (6) in order to drive the emitter (2)/detector (3) pair.

The system may be designed such that the whole assembly may be removed from the driving electronics and body of the capnometer, and may be replaced. Therefore, the breath tube assembly comprising curved reflector (4), optical layer (5) and emitter (2)/detector (3) printed on the circuit board (6) may be disposed after use of the capnometer.

While the aforementioned capnometers are suitable for purpose and enable high temporal resolution with high accuracy over a specific concentration range, the use of spherical/elliptical curved mirrors lead to a number of difficulties, including uneven heating leading to problems with condensation, the curvature of the mirror causing gas to be trapped in the apex reducing the temporal resolution of the system and the single path length meaning that the sensor is suited to only a narrow range of measurement. Furthermore, the curvature of the lens does not lend itself to easy introduction into a replaceable breath tube.

Figure 3:
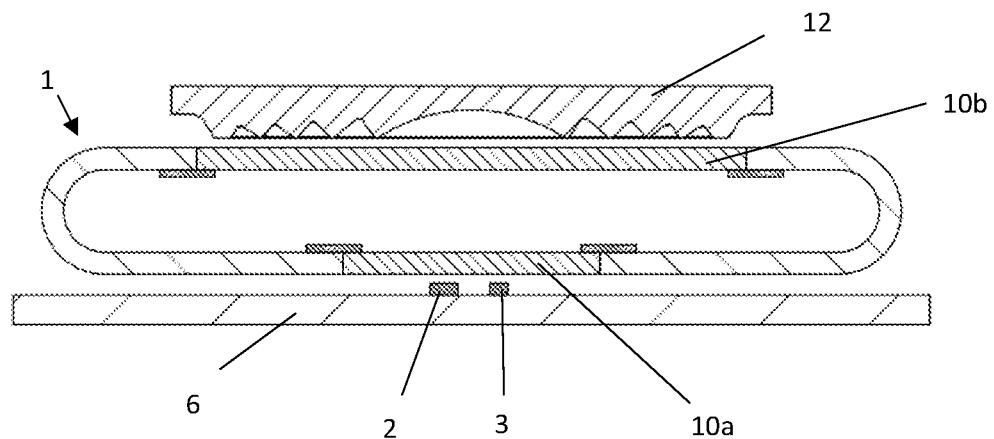
FIG. 3 shows a schematic illustration of a capnometer comprising a Fresnel reflector and a breath tube incorporating two IR-transmissive windows according to an embodiment of the present invention.

FIG. 3 of the accompanying drawings illustrates a capnometer according to one embodiment of the present invention. The capnometer incorporates a Fresnel reflecting lens (12) in place of the curved reflector (4). The capnometer comprises a breath tube (1) which constrains the air flow, the tube having incorporated into it one narrow and one relatively wide IR-transmissive window (10a, 10b) on opposing sides of the tube. The emitter (2) and detector (3) are provided adjacent the narrow window (10a) and are mounted on a printed circuit board (6). The Fresnel reflector (12) is provided behind the wider window (10b). The emitter/detector pair (1) may be composed of III-V semiconductors and suitable materials will be known to those skilled in the art. In this example the emitter is designed to emit IR radiation centred around 4.26 μm and the detector has a sensitivity peak centred around 4.26 μm. The emitter/detector pair and Fresnel lens will be aligned so that light emitted from emitter (2) is focused by the lens (12) on to the detector (3). The gas flows through the air region interposed between the emitter/detector pair (2,3) and the Fresnel reflector (12). The air flow region is isolated from the emitter/detector and the reflector by the silicon IR-transmissive windows (10a, 10b) which are provided with anti-reflections coatings and a heater (not shown).

The Fresnel reflector (12) is made from a high density polymer which may have been injection moulded. In the embodiment shown in FIG. 3 the Fresnel reflector contains five concentric elements, however there may be more or less elements. The reflector surface may be coated by evaporation, sputtering or other physical vapour deposition or via an electrochemical method with a thin metal film, such as silver, gold or aluminium. It will be appreciated that a variety of deposition techniques known to a skilled person may be exploited. In this example the reflector is coated with a gold film. However, it will be understood that a variety of other materials known to those skilled in the art may be used for this purpose.

The breath tube (1) is made from high-density polymer which may have been injection moulded and incorporate recesses for the silicon windows (10a, 10b) which may be bonded using a suitable adhesive. The silicon windows may have anti-reflection coatings to minimise the signal loss at the air/silicon interfaces. The silicon windows will also incorporate heaters to maintain a temperature of the window in contact with breath to minimise the effect of breath condensation on the optical path. Other materials for the optical windows transparent to infra-red radiation will be known to those skilled in the art and include but not limited to ZnS, ZnSe, Ge, chalcogenide glasses and certain polymers. The silicon window adjacent to the Fresnel lens (12) is placed in close proximity to the lens to limit the non-sampled gas volume.

Figure 4A:
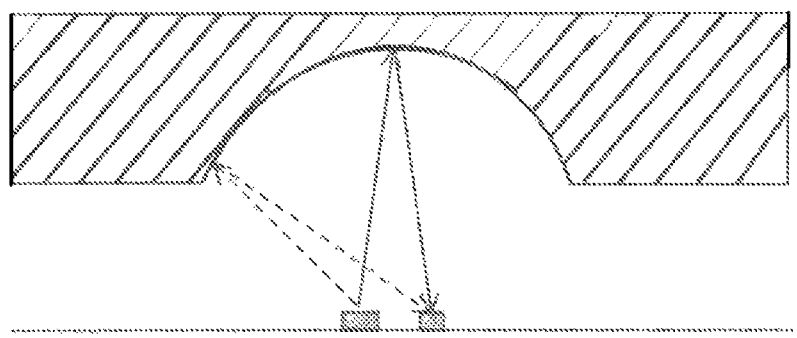
FIGS. 4A and 4B illustrate path lengths traversed by light rays from emitter to detector via a spherical reflector and a Fresnel lens reflector respectively.
Figure 4B:
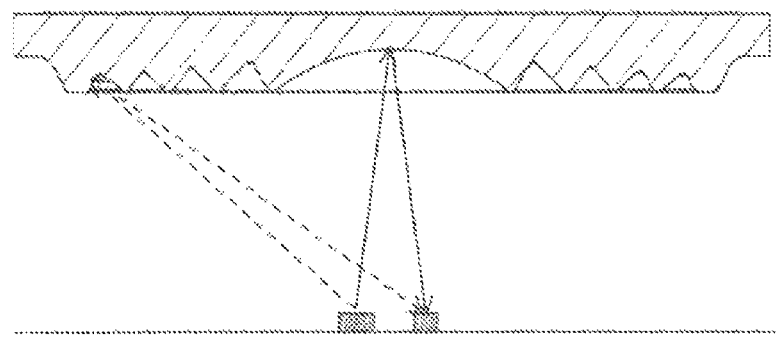

It should be appreciated that compared to a spherical reflecting geometry where the distance traversed by a light ray from emitter to detector via the reflector is substantially the same for all rays emitted at solid angles illuminating the reflector, the Fresnel lens (12) has a larger path length for rays emitted at larger angles (relative to the emitter surface normal direction), as illustrated in FIGS. 4A and 4B wherein FIG. 4A shows the path length for a spherical reflector and FIG. 4B shows the multiple path lengths for a Fresnel reflector. The sensitivity of the sensor is dependent on this path length. Measurements made at low gas concentrations require long path lengths to allow enough absorption of the ray to be detected and conversely, at high gas concentrations only small path lengths are required to prevent too small a signal being received by the detector. Therefore, there is an optimum path length required for a particular gas concentration. The range of carbon dioxide concentration in breath is large, therefore it is an advantage to have multiple path lengths as provided by the Fresnel lens incorporated into the capnometer of the present invention. Those skilled in the art can determine the optimum path length range in the gas being sampled depending on the power output of the emitter, the sensitivity of the detector and the losses in the optical path.

The use of the Fresnel lens reflector provides a number of advantages over the prior art. The flatter geometry allows the breath tube to be inserted with a smaller non-sampled dead space between the silicon window and the reflector thereby reducing the errors associated with the absorption of signal by gas in the dead space volume. The flat geometry also gives rise to a range of path lengths as detailed above, the consequence of which is to increase the range of measurement of the capnometer.

Figure 5:
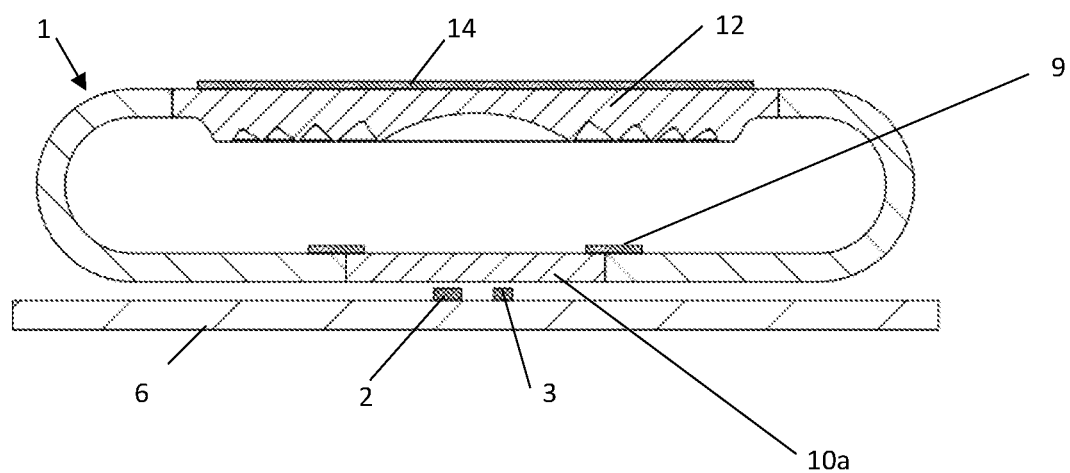
FIG. 5 shows a schematic illustration of a capnometer incorporating a Fresnel reflector within a disposable breath tube according to another embodiment of the present invention.

FIG. 5 illustrates a similar capnometer to that of FIG. 3 but having the Fresnel lens (12) provided as part of a replaceable breath tube (1). The emitter/detector pair (2,3) are again mounted on a PCB (6), the emitter (2) illuminating a gas flow region defined by the breath tube (1) incorporating a heated silicon window (10a) on the emitter/detector side and a Fresnel reflector (12) on the opposite side. The Fresnel reflector contains a heater (14) to prevent condensation affecting the signal focused by the Fresnel lens onto the detector. This arrangement not only provides for a higher signal level due to removal of reflection loss associated with the second silicon window (10b) but lowers the materials cost of the device. The heater enables the surfaces that are in contact with the sample gas to be heated so that the surface temperature is high enough to prevent condensation on the reflector (12) and/or the transmissive layer (10a). The flatter Fresnel reflector geometry enables the reflector to be heated more uniformly because a flat heater can be used, allowing it to be in more uniform contact with the surface to be heated. This enables the heater to use less energy, reducing the power consumption of the capnometer. Furthermore, the low heat energy requirement reduces the thermal expansion of the optical system, allowing it to maintain its optimum efficient geometry.

The breath tube (1) may be made from a high-density polymer which may have been injection moulded to form the required shape. The Fresnel lens is provided with an additional coating of material to achieve a reflecting surface as previously described in relation to FIG. 3. The Fresnel lens may be incorporated into the breath tube using a suitable adhesive or it may be fabricated in the same injection moulding tooling as the breath tube in two halves so that the side containing the Fresnel lens can be coated, the two halves subsequently attached using suitable adhesive or by interference fit. It can be appreciated that alignment features (not shown) are required to ensure that the breath tube (1) now incorporating the focussing element (12) can be aligned accurately to the emitter/detector pair (2,3).

The breath tube (1) may in embodiments contain channels which allow a sample gas to be diverted from the air flow region where the sample gas is examined, so that a conductance may be achieved which is high enough for the flow to be sampled.

Additionally, the surfaces of the reflector (12) and/or transmissive window (10a, 10b) which are in contact with the sample gas may be coated with materials which modify the surface energy. Hence, when water condensate from breath condenses on these surfaces, in the case of high surface energy modifiers, the water condensate forms a thin film rather than a droplet or droplets which potentially scatter and therefore reduce the IR radiation impinging on the detector (3). The surface energy modifying materials may be, but are not limited to, hydroxyl and carboxyl containing hydrocarbon thiols. Hydroxyl and carboxyl containing hydrocarbon thiols may be particularly suitable for coating a gold surface to form a self-assembled mono-layer. Poly-ethylene oxide or an amine of cyano containing polymers may be deposited on the surface of the reflector (12). In the case of low surface energy modifiers, the water condensate forms droplets that bead up and fall from the window, or in the case of the reflector (12) coat less of the reflector (12) and so have less effect on the signal. Low surface energy materials may be, but are not limited to fluoro-carbon containing molecules. Fluoro-carbon thiols may be particularly suitable for coating a gold surface using a self-assembled mono-layer.

Figure 6A:
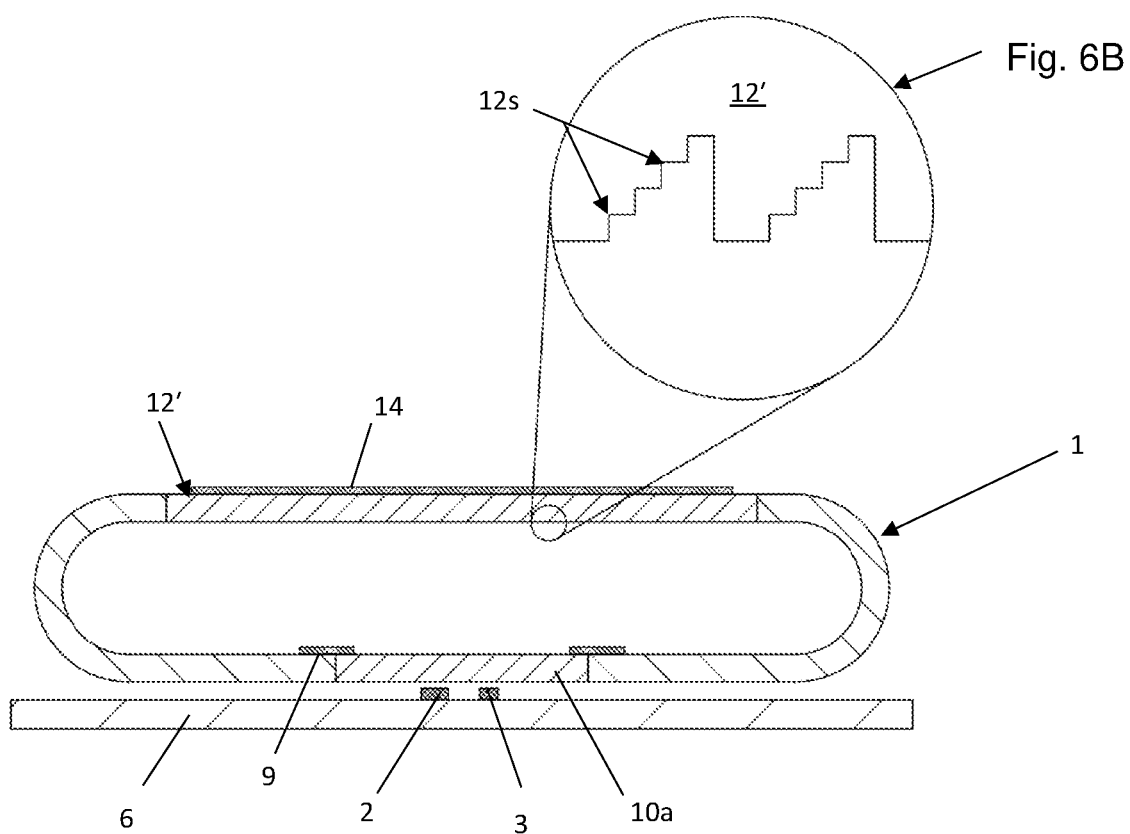
FIG. 6A shows a schematic illustration of a capnometer incorporating a Fresnel zone plate according to yet another embodiment of the present invention, with FIG. 6B being an expanded partial view of the Fresnel zone plate.

FIGS. 6A and 6B show a schematic of a capnometer according to another embodiment of the present invention. In this embodiment, the reflector comprises a reflective diffractive optical element in the form of a Fresnel Zone Plate "FZP" (12') of the multi-level type (see FIG. 6B) which is incorporated into the body of the removable breath tube (1). In this type of zone plate a series of steps (12s) that approximate to the continuous phase change introduced by a curved reflector can be made. The plate is again provided with a heater (14) and an IR transmissive window (10a) is provided opposite the plate in line with which are emitter (2) and detector (3) mounted on PCB (6). Typically, the series of steps (12s) introduce $<\pi/2$ phase change with no step height introducing greater than $2\pi$ of phase change therefore limiting the total height of the step and therefore limiting the total thickness of the mirror to this height plus any supporting thickness required to ensure mechanical integrity. For mid-infrared wavelengths the step heights are of the order of 0.5 μm and the total step heights are <5 μm.

The FZP may be fabricated using high-density polymer and injection moulding. It will be known by those skilled in the art that the injection moulding tooling for the small step heights required for multi-level phase FZPs suitable for infra-red wavelengths can be fabricated using silicon microfabrication techniques including but not limited to photolithography and etching of silicon dioxide and silicon nitride and silicon oxynitride layers grown by chemical vapour deposition (CVD) or plasma enhanced chemical vapour deposition (PECVD) on silicon. The master zone plate patterns may be used in the injection moulding tooling directly or be used to make an electroformed mould insert, typically using electroplated nickel. As for the Fresnel lens, the FZP requires coating with a reflective material.

Figure 7A:
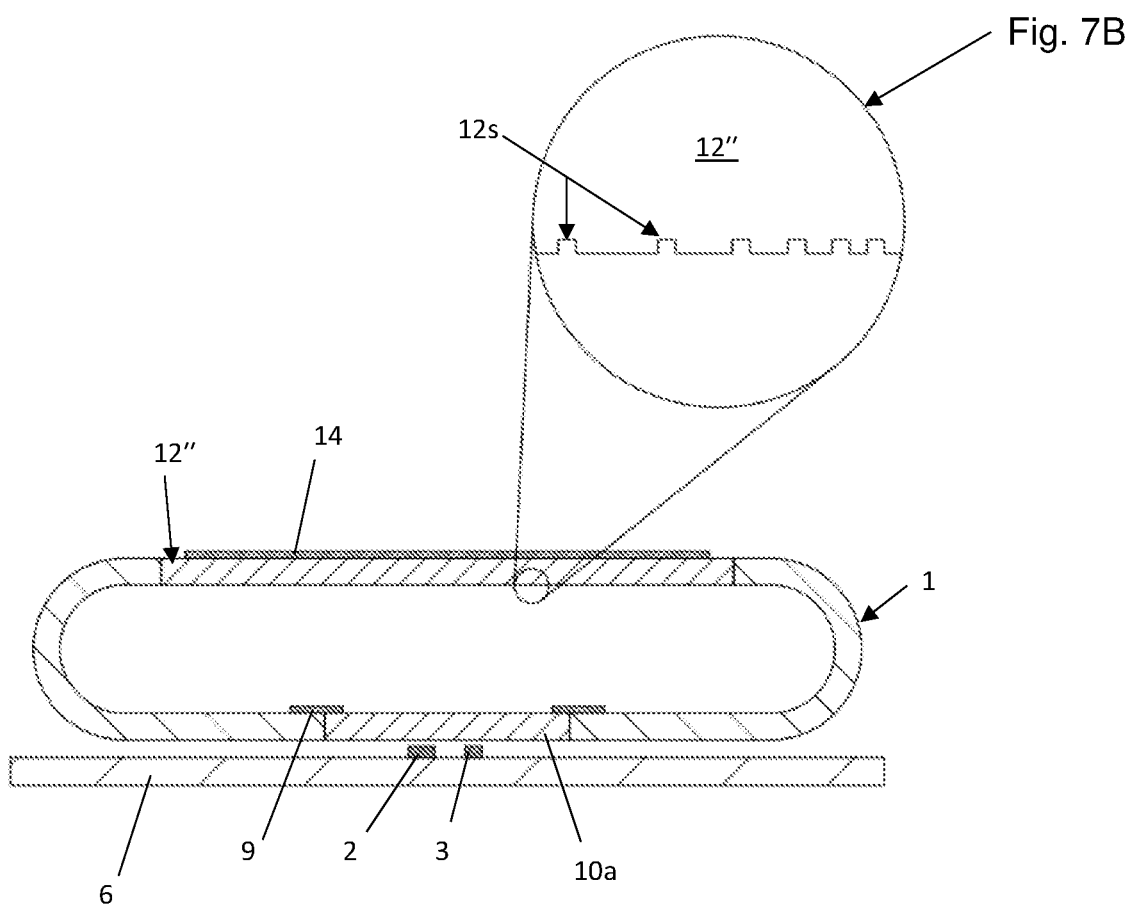
FIG. 7A shows a schematic illustration of a capnometer incorporating a Fresnel zone plate according to yet a further embodiment of the present invention, with FIG. 7B being an expanded partial view of the Fresnel zone plate.

FIGS. 7A and 7B show another embodiment of a capnometer according to the present invention incorporating a disposable breath tube (1) provided with a Fresnel Zone Plate "FZP" (12") with a single phase level (see FIG. 7B). This is one of the simplest diffracting elements with just one step height. In this embodiment, a series of concentric steps are patterned and coated with a suitable reflector such that the interference of wave fronts scattered from the surface of the zone plate (12) result in maximising of the flux of radiation on the detector (3). In the case where the FZP is separate to the breath tube the planar geometry also allows a breath tube to be inserted with minimum dead space, thereby minimising dead space error.

The pattern of steps is a set of concentric circles or ellipses optimised so that the phase of wavelets arriving at the detector are in substantially in-phase and those off the detector or out of phase. Various optimisations are known to those skilled in the art, where a particular pattern may also be referred to as a "photon sieve" or "hologram". Typically, the step height is one quarter of the wavelength of light, therefore this structure provides the thinnest optical element. Like the previous embodiments of FIGS. 3 and 5A to 6B, the structure requires a coating of reflective metal and can be fabricated by injection moulding of a high-density polymer using a suitable injection mould.

It is to be appreciated that in any of the aforementioned embodiments the capnometer may include a body (not shown), for example, of injection moulded high density polymer, in relation to which the breath tube is inserted. The body may contain locating pins which align to lugs in a printed circuit board. The Fresnel reflector (12) may optionally be integral to the body. The emitter (2)/detector (3) pair may be arranged on top of the printed circuit board and an electrical connector may be connected to the printed circuit board in order to drive the emitter (2)/detector (3) pair. The breath tube (1) may be interspersed between the moulded body and the printed circuit board.

In embodiments described herein, there is a problem of contamination of the reflective surface and/or any IR-transmissive windows/components. Contamination may reduce the signal received by the detector (3) and it may appear as an increase in $CO_2$ level even if no change has actually occurred. One method to mitigate this is to monitor the inspiration phase of the breath cycle where fresh air with low $CO_2$ levels is passed through the sampling area. Typically, the $CO_2$ concentration is approximately 450 ppm. It will be appreciated that the threshold may vary and may preferably be adjusted depending on conditions of the area surrounding the device. If the measured $CO_2$ level is higher than the threshold, the system may indicate that the measurement is void. A correction to the measured $CO_2$ level may be made.

Figure 8:
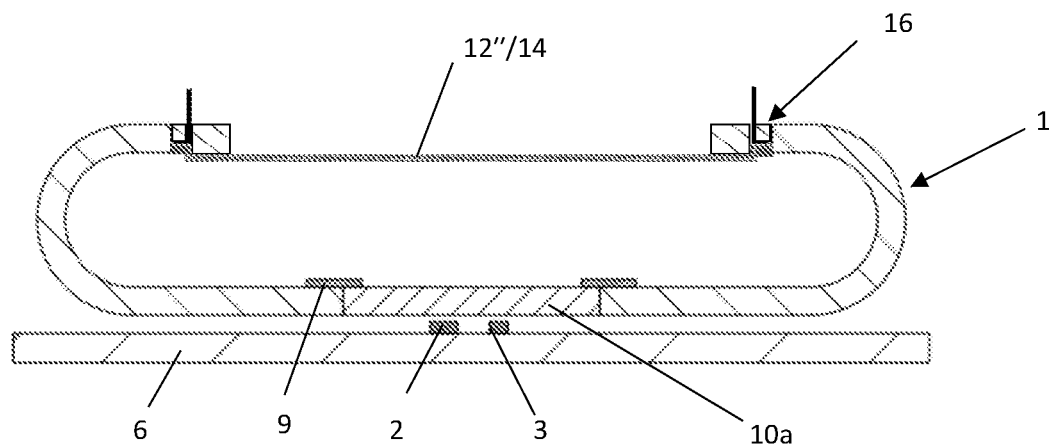
FIG. 8 shows a schematic illustration of a capnometer incorporating a thin film Fresnel zone plate with integral heater according to yet another embodiment of the present invention.

FIG. 8 shows another capnometer according to the present invention, the capnometer incorporating a breath tube (1) with a thin film single-level phase FZP focussing element (12") attached to the breath tube using a pre-formed recess and push-fit clip (16). The advantage of a film FZP is that it may be fabricated on a sheet using a hot embossing method. A foil which may be either of thin metal or polymer such as PET or PEN is coated with a thermosetting polymer capable of being moulded using a hot embossing roller. The foil can then be coated with a reflecting coating and the FZP cut from the foil. The FZP foil can incorporate a backside conducting element that may be attached to a current source using conductors. Not only is this method of FZP formation low cost it also has low thermal capacitance and so will use less power to heat the element to prevent condensation affecting the signal level received by the detector.

Figure 9:
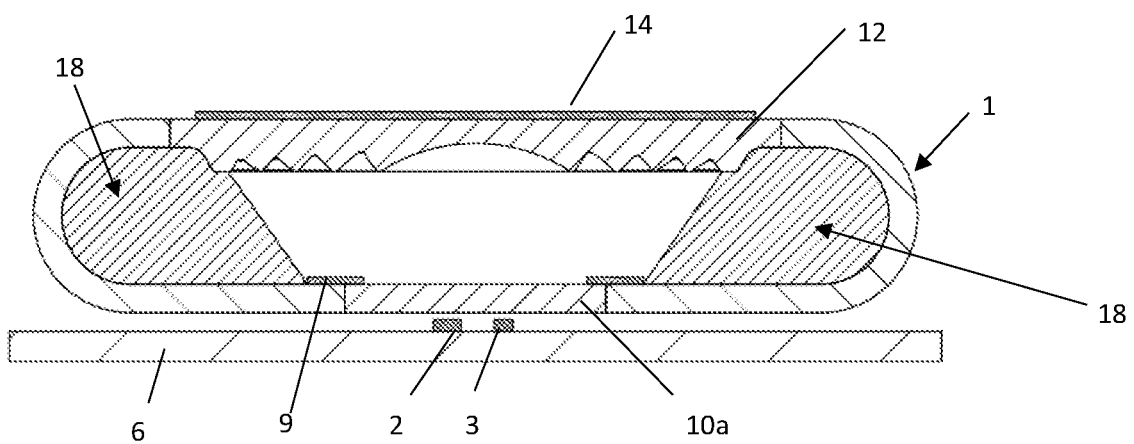
FIG. 9 is a cross-sectional view of a capnometer according to yet a further embodiment of the present invention.

FIG. 9 of the accompanying drawings, illustrates yet another embodiment of the present invention having a Fresnel reflector 12 provided within the breath tube (1) as shown in FIG. 5 but the breath pathway area is reduced by the provision of a restriction 18 between the emitter/detector (2,3) and the Fresnel lens (12). This serves to increase the velocity of the gas flowing through the sampling area, increasing a time-resolution of the determination of the concentration of the gas component to be determined. This increase in breath velocity ensures that the response time of the capnometer is not dependent on the transit time of breath in the sampling area.

In embodiments described herein, it may be necessary to add an additional mid-IR window between the emitter/detector pair and the breath tube to provide protection to these devices during replacement of the breath tube.

It is also necessary to achieve accurate calibration of the system. This is particularly the case where a replaceable breath tube (1) is employed since there is a possibility of small variations in alignment. The device may be calibrated assuming the background $CO_2$ level is known. This might be the case if the air is ambient air. Alternatively, the $CO_2$ level may be obtained from a different information source.

Alternatively, a breath tube (1) incorporating a gas of known $CO_2$ level may be used for calibrating the device. The breath tube (1) may comprise end caps which may have removable elements such that after calibration the removable elements may be peeled off and the device is ready to use.

No doubt many other effective alternatives will occur to the skilled person. It will be understood that the invention is not limited to the described embodiments and encompasses modifications apparent to those skilled in the art and lying within the spirit and scope of the claims appended hereto.

The invention claimed is:

1. A capnometer for detecting a concentration of a component in a gas, wherein the gas is inhaled and/or exhaled by a patient, the capnometer comprising:
   an air flow region through which the gas passes to and/or from the patient's lung;
   a mid-IR semiconductor emitter configured to provide IR light at a wavelength in the range 3-5 µm;
   a mid-IR semiconductor detector to detect the IR light and a reflector to reflect the IR light emitted by the emitter;
   wherein the emitter, the detector and the reflector are arranged such that the IR light emitted by the emitter passes through the air flow region via the reflector to the detector, wherein the capnometer further comprises:
   a breath tube that defines a channel between the emitter, the detector and the reflector, the channel defining the air flow region, the emitter and the detector being mounted adjacently on a circuit board on one side of the breath tube and the reflector being provided on an opposing side of the breath tube,
   wherein the reflector has a planar geometry,
   wherein the reflector is selected from the group consisting of a Fresnel reflector and a reflective diffractive optical element, and
   wherein the emitter and the detector are aligned such that light from the emitter is focused by the reflector onto the detector.

2. A capnometer as claimed in claim 1, wherein the breath tube is removable from the capnometer.

3. A capnometer as claimed in claim 1, wherein at least one of the emitter, the detector and the reflector are mounted in the breath tube.

4. A capnometer as claimed in claim 3, wherein the emitter and the detector are located external to the breath tube, and wherein the breath tube comprises a mid-IR transmissive portion, the mid-IR transmissive portion being aligned with the emitter and the detector to allow mid-IR light to pass therethrough into and out of the breath tube.

5. A capnometer as claimed in claim 1, wherein the breath tube comprises one or more alignment features for enabling the arrangement of the reflector with the emitter and the detector.

6. A capnometer as claimed in claim 1, wherein the emitter and the detector are located external to the breath tube, and wherein the breath tube comprises a mid-IR transmissive portion, the mid-IR transmissive portion being aligned with the emitter and the detector to allow mid-IR light to pass therethrough into and out of the breath tube and the reflector is located external to the breath tube, and wherein the breath tube comprises a second mid-IR transmissive portion, the second mid-IR transmissive portion being aligned with the reflector to allow mid-IR light to pass therethrough into and out of the breath tube.

7. A capnometer as claimed in claim 1, wherein the reflector is mounted in the breath tube.

8. A capnometer as claimed in claim 1, wherein the reflector is mounted in the breath tube and the breath tube is provided with preformed recesses for receipt of the reflector.

9. A capnometer as claimed in claim 1, wherein the reflector is mounted in the breath tube and a flat side of the reflector on an external side of the breath tube is in contact with a heater.

10. A capnometer as claimed in claim 1, wherein the reflector is a Fresnel reflector including at least one cut in at least one concentric ring.

11. A capnometer as claimed in claim 1, wherein the reflector is a reflective diffractive optical element in the form of a Fresnel zone plate, reflective grating or reflective hologram, the reflective diffractive optical element including at least one step.

12. A capnometer as claimed in claim 11, wherein the reflector is a Fresnel zone plate of multiple phase levels, the plate having a series of steps of more than one step height, wherein the step heights introduce $<\pi/2$ phase change with no step height introducing greater than $2\pi$ of phase change.

13. A capnometer as claimed in claim 11, wherein the reflector is a Fresnel zone plate of multiple phase levels, the plate having a series of steps of more than one step height, wherein the step heights are <0.5 μm and the total step heights are <5 μm.

14. A capnometer as claimed in claim 11, wherein the reflector is a Fresnel zone plate, reflective grating or reflective hologram of a single phase level comprising a series of steps of a single height, wherein the height of each step is around one quarter the wavelength of light.

15. A capnometer as claimed in claim 11, wherein the reflector is provided as a thin film single level phase FZP focussing element.

16. A capnometer as claimed in claim 11, wherein the reflector is provided as a thin film single level phase FZP focussing element and further comprises a backside conducting element provided on the thin film.

17. A capnometer as claimed in claim 11, wherein the at least one step comprises multiple steps.

18. A capnometer as claimed in claim 1, further comprising a diversion device for blocking one of a first and a second air-flow path in the capnometer at a time,
wherein the first air-flow path connects an inhaling/exhaling portion of the capnometer at which a user of the capnometer inhales/exhales air and an intake portion of the capnometer through which air enters the capnometer, and
wherein the second air-flow path connects the inhaling/exhaling portion and an exit portion of the capnometer at which air exits the capnometer.

19. An inhaler comprising a capnometer according to claim 1, wherein the capnometer is configured to monitor a $CO_2$ level in air inhaled through or exhaled through the inhaler.

20. A capnometer as claimed in claim 10, wherein the at least one cut in at least one concentric ring comprises multiple cuts in multiple concentric rings.

* * * * *